United States Patent
Marsh (10) Patent No.: US 9,381,523 B2
(45) Date of Patent: Jul. 5, 2016

(54) AUTOMATED FRACTION COLLECTION SYSTEM

(75) Inventor: Blaine J. Marsh, Columbia, NJ (US)

(73) Assignee: Alfa Wassermann, Inc., West Caldwell, NJ (US)

( * ) Notice: Subject to any disclaimer, the term of this patent is extended or adjusted under 35 U.S.C. 154(b) by 1085 days.

(21) Appl. No.: 13/306,158

(22) Filed: Nov. 29, 2011

(65) Prior Publication Data

US 2012/0068069 A1    Mar. 22, 2012

Related U.S. Application Data

(62) Division of application No. 11/608,304, filed on Dec. 8, 2006, now Pat. No. 8,083,662.

(60) Provisional application No. 60/749,207, filed on Dec. 9, 2005.

(51) Int. Cl.
| | | |
|---|---|---|
| *G01N 21/85* | (2006.01) | |
| *B04B 11/04* | (2006.01) | |
| *B04B 13/00* | (2006.01) | |
| *G01F 23/292* | (2006.01) | |
| *G01N 1/18* | (2006.01) | |
| *G01F 11/28* | (2006.01) | |

(Continued)

(52) U.S. Cl.
CPC ............ *B04B 11/04* (2013.01); *B04B 13/00* (2013.01); *G01F 11/284* (2013.01); *G01F 11/44* (2013.01); *G01F 23/2921* (2013.01); *G01N 1/18* (2013.01); *G01N 1/40* (2013.01)

(58) Field of Classification Search
CPC ....... G01N 21/35; G01N 21/05; G01N 21/07; G01N 21/11; G01N 21/17; B01L 3/0237; B01L 2300/0627

USPC ................. 422/501, 509, 517–518, 520–521; 73/863.32, 863.86, 864, 864.01, 73/864.02, 864.11, 864.15, 427
See application file for complete search history.

(56) References Cited

U.S. PATENT DOCUMENTS

| | | |
|---|---|---|
| 3,007,629 A | 11/1961 | Boyland |
| 3,107,818 A | 10/1963 | Carmellini et al. |

(Continued)

FOREIGN PATENT DOCUMENTS

| | | |
|---|---|---|
| JP | 2006021121 | 1/2006 |

OTHER PUBLICATIONS

European Search Report dated Jun. 16, 2011 for European application No. 06848523.4.

(Continued)

*Primary Examiner* — Brian R Gordon
(74) *Attorney, Agent, or Firm* — Ohlandt, Greeley, Ruggiero & Perle, L.L.P.

(57) ABSTRACT

A system for separating a sample and collecting the separated sample. The system includes an ultracentrifuge having a cylindrical rotor. The system includes a gradient delivery assembly for delivering a gradient solution to the ultracentrifuge rotor, and a sample delivery assembly for delivering the solution containing the sample to the ultracentrifuge rotor. The system includes a fraction collection assembly for collecting discrete volumes of the separated sample. The system includes a processor for controlling operation of the ultracentrifuge, as well as the gradient delivery assembly, the sample delivery assembly, and/or the fraction collection assembly.

13 Claims, 6 Drawing Sheets

(51) Int. Cl.
*G01F 11/44* (2006.01)
*G01N 1/40* (2006.01)

(56) References Cited

U.S. PATENT DOCUMENTS

| | | | |
|---|---|---|---|
| 3,108,955 A | 10/1963 | Boyland | |
| 3,430,849 A | 3/1969 | Nunley | |
| 3,636,360 A | 1/1972 | Oishi et al. | |
| 3,908,441 A | 9/1975 | Virloget | |
| 4,638,925 A | 1/1987 | Buchner et al. | |
| 5,331,850 A * | 7/1994 | Loos | 73/293 |
| 5,551,940 A | 9/1996 | Cote | |
| 5,660,727 A | 8/1997 | Gleave et al. | |
| 5,922,211 A | 7/1999 | Nees | |
| 6,177,014 B1 | 1/2001 | Potter et al. | |
| 6,773,673 B1 * | 8/2004 | Layfield et al. | 422/81 |
| 7,144,361 B2 | 12/2006 | Aizawa et al. | |
| 7,396,324 B2 | 7/2008 | Tetsu et al. | |
| 7,591,775 B2 | 9/2009 | Tobita et al. | |
| 7,628,956 B2 * | 12/2009 | Jindo | F04B 11/0075 324/71.4 |
| 7,803,635 B1 * | 9/2010 | Meece | 436/181 |
| 8,446,586 B2 * | 5/2013 | Wu | C12N 5/0667 250/339.01 |
| 2002/0132354 A1 | 9/2002 | Downs et al. | |
| 2003/0114289 A1 | 6/2003 | Merino et al. | |
| 2004/0214711 A1 | 10/2004 | Aizawa et al. | |
| 2005/0107235 A1 | 5/2005 | Tetsu et al. | |
| 2006/0009341 A1 | 1/2006 | Tobita et al. | |
| 2006/0105462 A1 * | 5/2006 | Sellek-Prince | 436/55 |
| 2007/0142197 A1 | 6/2007 | Marsh | |
| 2008/0251436 A1 | 10/2008 | Tetsu et al. | |
| 2009/0239729 A1 | 9/2009 | Tobita et al. | |
| 2009/0299018 A1 * | 12/2009 | Oka et al. | 526/71 |
| 2011/0081281 A1 * | 4/2011 | Ludwig | 422/509 |

OTHER PUBLICATIONS

International Search Report dated Nov. 19, 2007 for PCT application No. PCT/US2006/046860.
Canadian Office Action dated Apr. 1, 2014 for Canadian patent application No. 2,838,160.
European Office Action dated Oct. 19, 2013 for European application No. 06848523.4.
Canadian Office Action dated Mar. 24, 2015 for Canadian patent application No. 2,838,160.
Extended European Search Report dated April 2 6, 2016 from corresponding EP Application No. 15186333.9, 7 pages.

* cited by examiner

AUTOMATED FRACTION COLLECTION SYSTEM

CROSS REFERENCE TO RELATED APPLICATIONS

This application is a divisional U.S. application Ser. No. 11/608,304 filed Dec. 8, 2006, which issued as U.S. Pat. No. 8,083,662, which claims the benefit of U.S. Provisional Application Ser. No. 60/749,207, filed Dec. 9, 2005, the entire contents of all of which are incorporated herein by reference.

BACKGROUND OF THE INVENTION

1. Field of the Invention

The present disclosure relates generally to a fraction collection system, and more particularly to an automated system permitting separation, enrichment and fractionation of subcellular particles.

2. Description of Related Art

Characterization of biological materials, such as biological molecules and organelles, has become increasingly important. Precise characterization of these materials can lead to novel drug therapies for treating disease, as well as to a greater understanding of the mechanisms underlying many diseases. Many biological materials exhibit a buoyant density that can be used to distinguish them from other materials. Such materials can be separated using density gradients and procedures such as differential centrifugation. For example, lipoproteins are composed of varying amounts of proteins and lipids. They differ not only by size and electrophoretic mobility, but also by buoyant density. Thus, in addition to other techniques available for separating, identifying, and classifying lipoproteins, density-gradient ultracentrifugation may be used. Such methodologies are complicated and time consuming particularly when minute fractions of large samples are being analyzed. Thus, there is a need for an automated method of isolating biological materials that can be used with smaller or larger samples and a method that is capable of segregating dilute materials from large samples.

SUMMARY

Briefly, the present invention includes a system for separating a sample and collecting the separated sample. The system comprises an ultracentrifuge having a cylindrical rotor sized and shaped for holding a solution containing the sample and spinning the solution to separate the sample contained in the rotor according to its buoyant density. The system also comprises a gradient delivery assembly connected to the ultracentrifuge for delivering a gradient solution to the ultracentrifuge rotor, and a sample delivery assembly connected to the ultracentrifuge for delivering the solution containing the sample to the ultracentrifuge rotor. In addition, the system includes a fraction collection assembly connected to the ultracentrifuge for collecting discrete volumes of the separated sample. Further, the system comprises a processor for controlling operation of the ultracentrifuge and at least one assembly of a group of assemblies consisting of the gradient delivery assembly, the sample delivery assembly, and the fraction collection assembly.

In another aspect, the invention includes a fraction volume measurement assembly for measuring and dispensing a predetermined volume of a sample. The assembly comprises a measurement tube having a lower end and an upper end. The lower end includes an opening for permitting the sample to enter and leave the tube. The assembly also comprises a valve in communication with the opening in the lower end of the measurement tube for controlling flow of the sample into and out of the tube. Further, the assembly comprises an electromagnetic transmitter mounted on the tube for transmitting electromagnetic energy along a line, and an electromagnetic receiver mounted on the tube opposite the transmitter and along the line of transmitted electromagnetic energy so that when an upper level of the sample in the tube is below the line, energy transmitted by the transmitter is received by the receiver and when an upper level of the sample in the tube is above the line, the transmitted energy is retracted so it is not received by the receiver, indicating the predetermined volume of the sample is present in the tube.

In yet another aspect, the invention includes a fraction collection assembly for collecting fractions having predetermined volumes. The assembly comprises a measurement tube having a lower end and an upper end. The lower end includes an opening for permitting the sample to enter and leave the tube. The assembly also comprises a valve in communication with the opening in the lower end of the measurement tube for controlling flow of the sample into and out of the tube, and an infrared sensor mounted adjacent the tube for determining when a predetermined volume of sample is present in the tube.

In still another aspect, the invention includes a processor for automatically controlling operation of a system including an ultracentrifuge having a rotor for containing and spinning a solution to separate particles in the solution according to their buoyant density, a solution delivery assembly connected to the ultracentrifuge for delivering a solution to the ultracentrifuge rotor, and a sample delivery assembly connected to the ultracentrifuge for delivering the solution containing the particles to the ultracentrifuge rotor. The processor provides commands to the system to perform a method comprising filling the rotor of the ultracentrifuge with buffer solution, and eliminating air from the rotor of the ultracentrifuge. The method also comprises filling at least a portion of the rotor of the ultracentrifuge with gradient solution, rotating the rotor to a predetermined speed, and loading a sample solution into the rotating rotor. In addition, the method comprises recycling eluent through the rotating rotor, stopping the rotor, drawing solution from a lower end of the stopped rotor, and indexing a receptacle having a series of wells to sequentially collect the solution from the lower end of the rotor in the wells.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
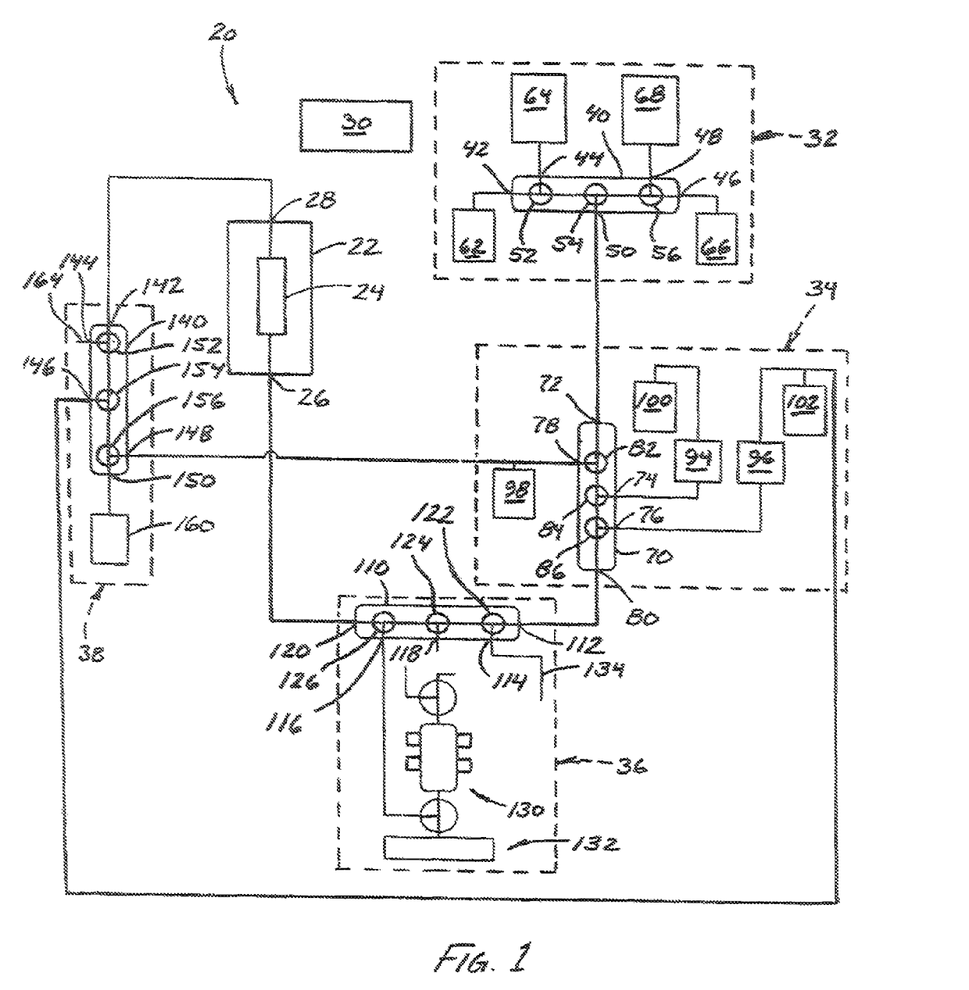
FIG. 1 is a schematic diagram of a system of the present invention.

Referring now to the drawings and in particular to FIG. 1, a system of the present invention is designated in its entirety by the reference numeral 20. The system 20 includes an ultracentrifuge 22 having a cylindrical rotor 24 that spins about a vertically-oriented axis at high speeds (e.g., speeds as high as 35,000 revolutions per minute (rpm) or more) to separate particles contained in solution in the rotor according to their buoyant density. The rotor 24 has a sample port 26 at its lower end through which samples are introduced and withdrawn. An overflow port 28 is provided at an upper end of the rotor 24. An electric motor (not shown) controlled by a processor 30 is used to spin the rotor 24. Although other processors may be used without departing from the scope of the present invention, in one embodiment the processor is a CFP-2020 compact field point network module available from National Instruments Corporation of Austin, Tex. As will be appreciated by those skilled in the art, the processor 30 may include a main processor and one or more input-output processors or modules. The ultracentrifuge 22 may also include a cooling system (not shown) to maintain components of the ultracentrifuge within operating limits. Although other ultracentrifuges 22 may be used without departing from the scope of the present invention, in one embodiment the ultracentrifuge is a pCFU ultracentrifuge available from Alfa Wassermann, Inc. of West Caldwell, N.J. Because other features of the ultracentrifuge 22 are well known to those skilled in the art, they will not be described in further detail.

The system also includes a solution delivery assembly 32, a sample delivery assembly (generally designated by 34), a fraction collection assembly (generally designated by 36) and an overflow management assembly (generally designated by 38). The solution delivery assembly 32 includes a manifold 40 having five ports 42, 44, 46, 48, 50 that are selectively connected by three interconnected 3-way servo-driven stopcocks or valves 52, 54, 56. As will be appreciated by those skilled in the art, each of the stopcocks 52, 54, 56 includes a generally cylindrical body having passages forming a tee-intersection. The stopcocks 52, 54, 56 may be rotated to align the passages so they are connected to selected ports 42, 44, 46, 48, 50. Each of the stopcocks 52, 54, 56 is driven between the various rotational positions by a corresponding servomotor that is connected to the processor 30. Although other manifolds may be used without departing from the scope of the present invention, in one embodiment the manifold 40 is a unit containing three ganged stopcocks available from Elcam Medical Inc. of Hackensack, N.J. Each of the stopcocks is driven by a HSR-5997TG servomotor available from Hitec RCD USA, Inc. of Poway, Calif. As will be appreciated by those skilled in the art, the servomotors position may be controlled by a pulse width modulated signal sent to an embedded controller. Confirmation that the servomotor reached the predetermined position is achieved by monitoring the electrical current drawn by the servomotor. The current approaches zero as the servomotor approaches the predetermined position. Because other features of the manifold 40 are well known to those skilled in the art, they will not be described in further detail. Port 42 is connected to a gradient reservoir 62 containing an appropriate gradient solution such as a 60% sucrose solution. Port 44 is connected to a motor-driven gradient syringe 64 having a barrel and a plunger slidably mounted in the barrel for selectively drawing gradient solution into the barrel and forcing the gradient solution out of the barrel. Port 46 is connected to a buffer reservoir 66 containing an appropriate buffer solution such as an 8% sucrose solution. Port 48 is connected to a motor-driven buffer syringe 68 having a barrel and a plunger similar to those of the gradient syringe 64 for selectively drawing buffer solution into the barrel and forcing the buffer solution out of the barrel. Both plungers of the gradient syringe 64 and the buffer syringe 68 may be driven between the various positions by a corresponding stepper motor connected to the processor 30. Although other automated syringes may be used without departing from the scope of the present invention, in one embodiment the gradient syringe 64 and the buffer syringe 68 are 009760 100 ml glass syringes available from SGE, Incorporated of Austin Tex., driven by PK246PB stepper motors available from Oriental Motor U.S.A. Corp. of Torrance, Calif. Port 50 forms an outlet port for the solution delivery assembly 32.

The sample delivery assembly 34 includes a manifold 70 similar to the manifold 40 of the solution delivery assembly 32. The manifold 70 has five ports 72, 74, 76, 78, 80 that are selectively connected by three interconnected 3-way servo-driven stopcocks 82, 84, 86 controlled by the processor 30. Because the manifold 70 of the sample delivery assembly 34 is similar to the manifold 40 of the solution delivery assembly 32, it will not be described in further detail. The outlet port 50 of the solution delivery assembly 32 is connected to port 72 of the sample deliver assembly manifold 70. Port 74 is connected to a peristaltic sample pump 94, and port 76 is connected to a peristaltic recycle pump 96. Both the sample pump 94 and the recycle pump 96 are controlled by the processor 30. Although other pumps may be used without departing from the scope of the present invention, in one embodiment both the sample pump 94 and the recycle pump 96 are 040.NP10.4DO-100 RPM 314 VDL/D peristaltic pumps available from Watson-Marlow Bredel Inc. of Wilmington, Mass. Because the pumps 94, 96 are conventional, they will not be described in further detail. Port 78 is connected to a waste reservoir 98, and port 80 forms an outlet port for the sample delivery assembly 34. The sample pump 94 is connected to a sample reservoir 100 containing an appropriate sample to be separated such as a protein solution. The recycle pump 96 is connected to a recycle reservoir 102.

The fraction collection assembly 36 includes a manifold 110 similar to the manifold 40 of the solution delivery assembly 32. The manifold 110 has five ports 112, 114, 116, 118, 120 that are selectively connected by three interconnected 3-way servo-driven stopcocks 122, 124, 126 controlled by the processor 30. Because the manifold 110 of the fraction collection assembly 36 is similar to the manifold 40 of the solution delivery assembly 32, it will not be described in further detail. The outlet port 80 of the sample delivery assembly 34 is connected to port 112 of the fraction collection assembly manifold 110. Port 114 is connected to a priming accumulator 134. Port 116 is connected to a fraction volume measurement assembly, generally designated by 130, that is connected to a fraction collector, generally designated by 132. Although other fraction collectors may be used without departing from the scope of the present invention, in one embodiment the collector 132 is a motor driven stage which receives a collection receptacle having a plurality of wells arranged in a grid. The position of the stage is controlled by the processor 30. Although the Because stages and receptacles of this type are known in the art, they will not be described in further detail. Port 118 is capped to provide future system expansion. Port 120 forms an outlet port of the fraction collection assembly 36 and is connected to sample port 26 of the ultracentrifuge rotor 24.

The overflow management assembly 38 includes a manifold 140 similar to the manifold 40 of the solution delivery assembly 32. The manifold 140 has five ports 142, 144, 146, 148, 150 that are selectively connected by three interconnected 3-way stopcocks 152, 154, 156 driven by servomotors connected to the processor 30. Because the manifold 140 of the overflow management assembly 38 is similar to the manifold 40 of the solution delivery assembly 32, it will not be described in further detail. The overflow port 28 of the ultracentrifuge rotor 24 is connected to port 142 of the overflow management assembly manifold 140. Port 144 is connected to a vent 164. Port 146 is connected to the recycle reservoir 102 of the sample delivery assembly 34. Port 148 is connected to the waste reservoir 98, which is connected to port 78 of the sample delivery assembly manifold 70. Port 150 is connected to a final flow reservoir 160.

Figure 2:
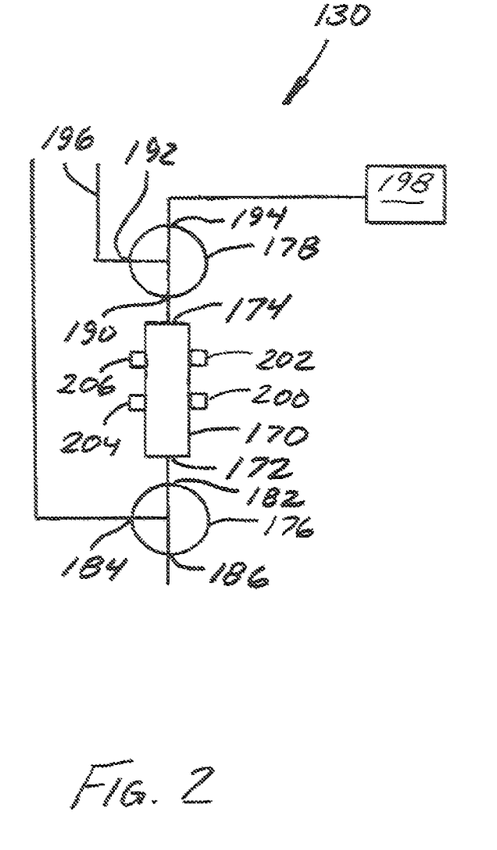
FIG. 2 is a schematic diagram of a fraction volume measurement assembly of the present invention.

As illustrated in FIG. 2, the fraction volume measurement assembly 130 includes a transparent central tube 170 having a lower end 172 and an upper end 174. Although the tube 170 may have other shapes and dimensions without departing from the scope of the present invention, in one embodiment the tube 170 has an inner diameter of about ten millimeters. A 3-way servo-driven stopcock 176 is positioned at the lower end 172 of the tube 170 and a 3-way servo-driven stopcock 178 is positioned at the upper end 174 of the tube 170. The lower stopcock 176 has ports 182, 184, 186. Port 182 is connected to the lower end 172 of the central tube 170. Port 184 is connected to port 120 of the fraction collection assembly manifold 110, and port 186 drains into the fraction collector 132. The upper stopcock 178 has ports 190, 192, 194. Port 190 is connected to the upper end 174 of the central tube 170. Port 192 is connected to a vent line 196 and port 194 is connected to a lower pressure pas source 198. Although the gas source 198 may be at other pressures without departing from the scope of the present invention, in one embodiment the gas source pressure is between about 1 pounds per square inch (psi) and about 3 psi. Although the gas source 198 may include other gases without departing from the scope of the present invention, in one embodiment the gas source provides filtered clean air.

A pair of infrared transmitters 200, 202 are provided on one side of the central tube 170, and a pair of corresponding infrared receivers 204, 206 are provided on the side of the tube opposite the transmitters. When solution inside the central tube 170 rises to a level high enough that it extends above a line between transmitter 200 and receiver 204, the infrared signal produced by the transmitter is refracted so it does not reach the receiver. The receiver 204 sends a signal to the processor 30 indicating a corresponding level in the tube 170 has been reached and the solution in the tube has reached a corresponding volume. As will be appreciated by those skilled in the art, a volume of the tube 170 below this signal level may be adjusted by moving the transmitter and receiver pair. As will further be appreciated, the second transmitter 202 and receiver 206 may be used to measure a second predetermined solution volume. Although other transmitters and receivers may be used without departing from the scope of the present invention, in one embodiment the transmitters and receivers are photomicrosensors such as an EE-SPX613 photomicrosensor available from Omron Electronics LLC of Schaumburg, Ill.

Figure 3:
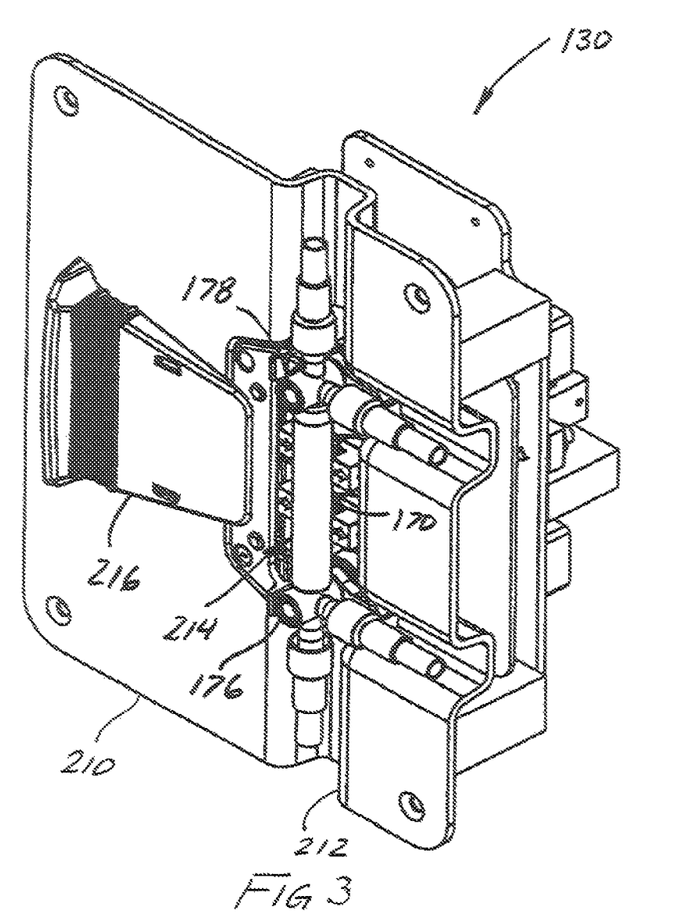
FIG. 3 is a perspective of a fraction volume measurement assembly.
Figure 4:
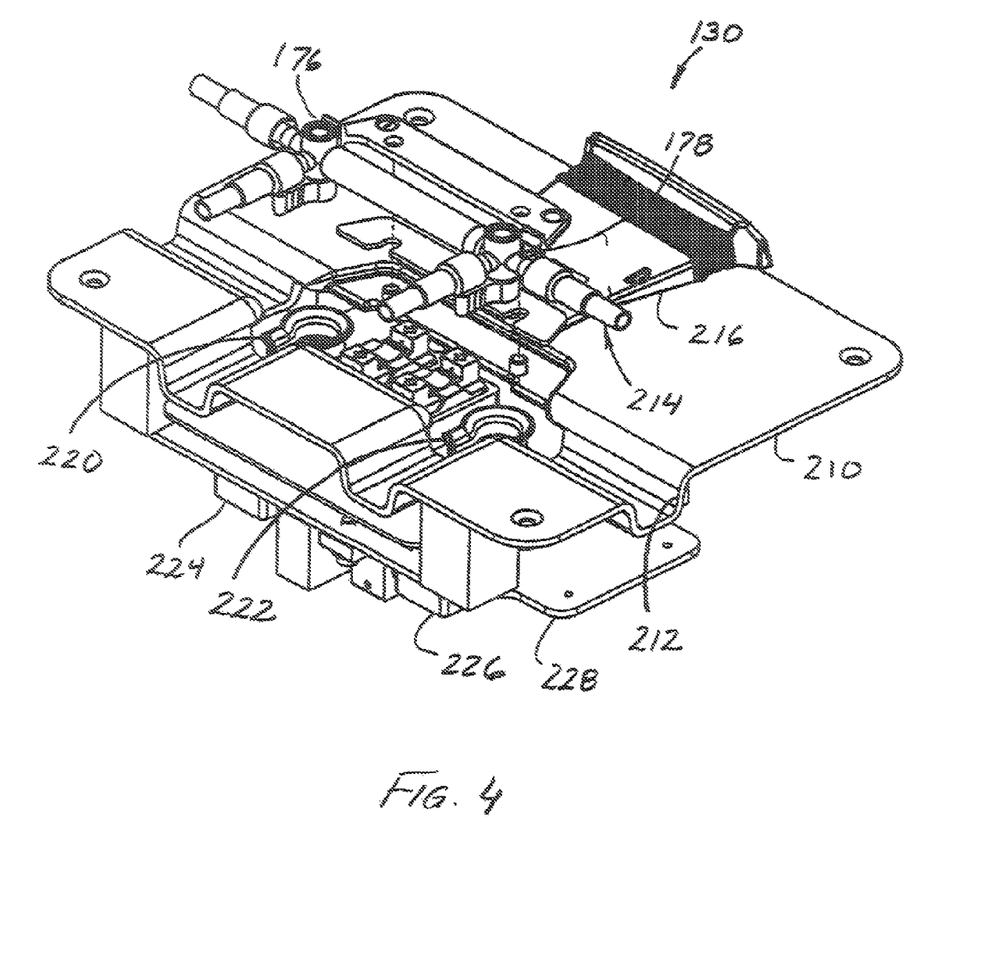
FIG. 4 is a perspective of the fraction volume measurement assembly shown in FIG. 3 rotated and partially disassembled.
Figure 5:
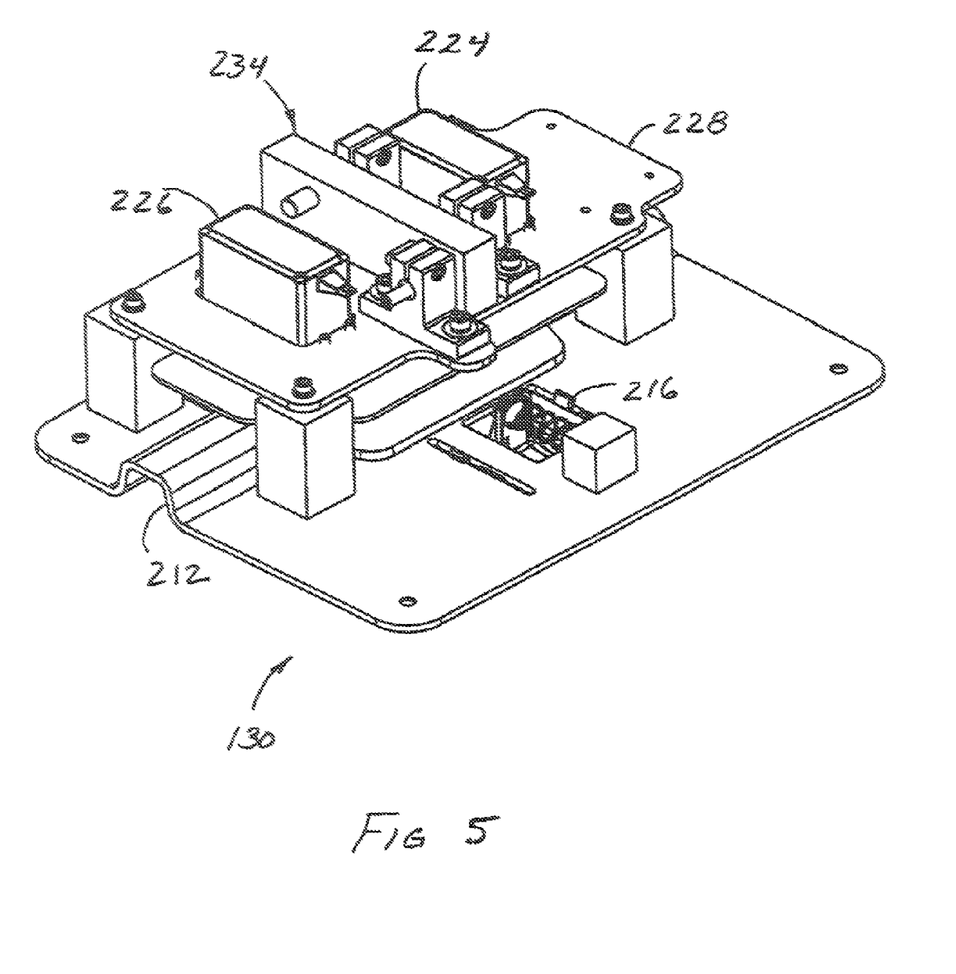
FIG. 5 is a rotated perspective of the assembly shown in FIG. 3.
Figure 6:
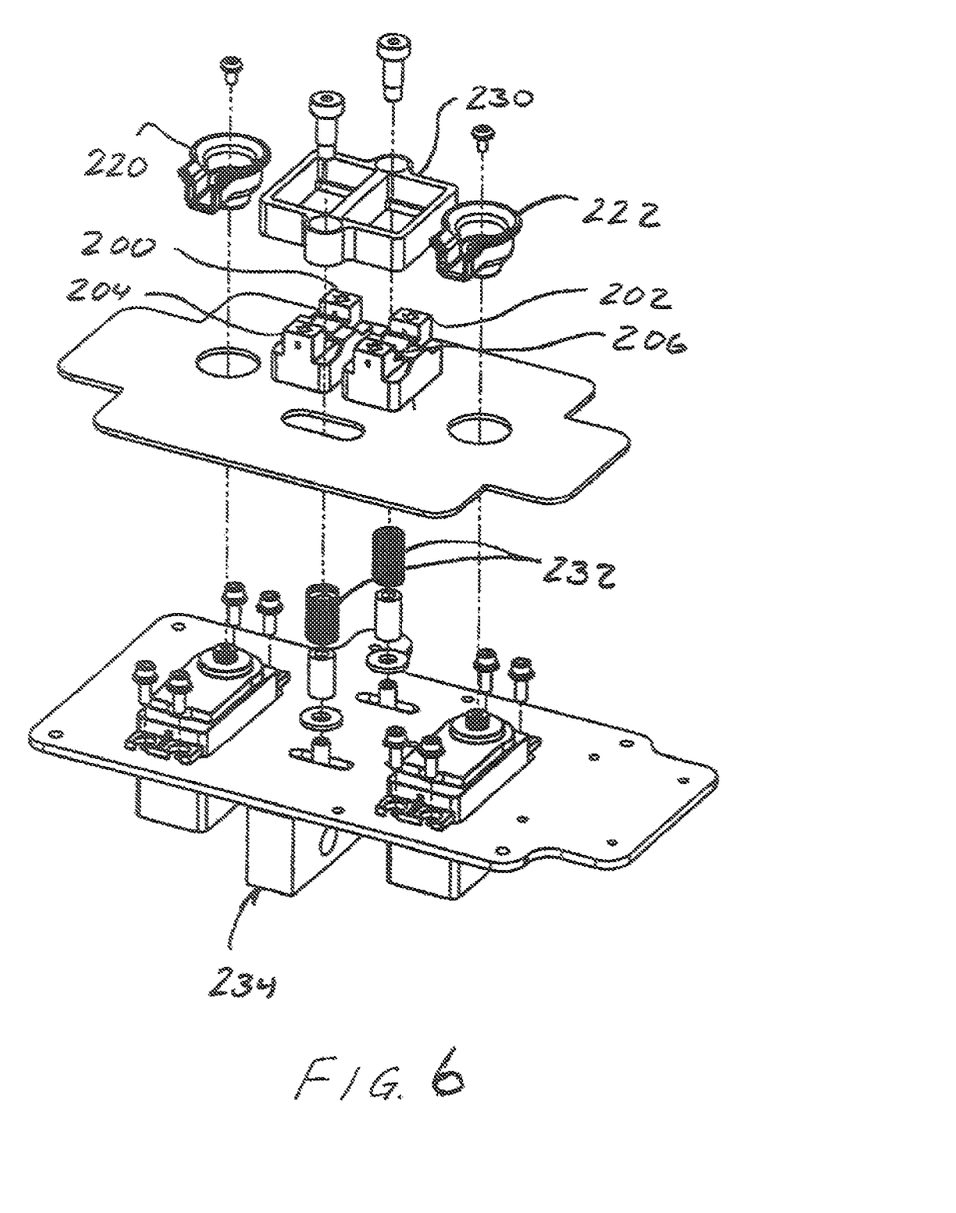
FIG. 6 is a separated view of a portion of the fraction volume measurement assembly.

As shown in FIG. 3, the fraction volume measurement assembly 130 comprises a base plate 210 having a recess 212 for receiving a separable tube and stopcock sub-assembly, generally designated by 214, which includes the central tube 170 and stopcocks 176, 178. Although other tube and stopcock sub-assemblies may be used without departing from the scope of the present invention, in one embodiment the sub-assemblies are specially made by Elcam Medical Inc. of Hackensack, N.J. A spring loaded clamp 216 is provided on the base plate 210 for holding the tube and stopcock sub-assembly 214 in position in the recess 212. As illustrated in FIG. 4, the assembly 130 includes cups 220, 222 adapted to receive levers on the stopcocks 176, 178, respectively, when the sub-assembly 214 is in position in the recess 212. The cups 220, 222 are rotated by corresponding servomotors 224, 226 mounted on a bracket 228 connected to the base plate 210. FIG. 5 provides an alternate view of the servomotors 224, 226 and bracket 228. As illustrated in FIG. 6, the infrared transmitters 200, 202 and receivers 204, 206 are held in a mount 230. The mount 230 is biased by springs 232 toward the tube and stopcock sub-assembly 214 when it is positioned in the recess 212. Further, the mount 230 is fixed to an adjustment mechanism, generally designated by 234 (FIG. 5), which permits the positions of the transmitters 200, 202 and receivers 204, 206 to be adjusted relative to the tube and stopcock sub-assembly 214, permitting adjustment of the volume measured by the assembly 130.

The processor 30, which may include programs embedded in hardware and/or software, is adapted to produce a series of commands for controlling the operation of the system 20 and components thereof. During a first operation, passages in the components of the solution delivery assembly 32 and the sample delivery assembly 34 that carry the gradient solution are purged of foreign materials. The processor 30 commands the solution delivery assembly manifold stopcocks 52, 54, 56 to rotate so that port 42 is in communication with port 44. The processor 30 then commands the motor-driven gradient syringe 64 to pull the syringe plunger to aspirate a predetermined volume (e.g., 20 milliliters (ml)) of gradient solution from the gradient reservoir 62. The volume of gradient solution aspirated into the syringe barrel should be sufficient to fill the passages in the components of the solution delivery assembly 32 and the sample delivery assembly 34 that carry the gradient solution. Once an appropriate volume of gradient solution is aspirated, the processor 30 commands the stopcocks 52, 54, 56 of the solution delivery assembly 32 to rotate so that port 44 is in communication with the outlet port 50 and the stopcocks 82, 84, 86 of the sample delivery assembly 34 to rotate so that port 72 is in communication with port 78. Once these connections are made, the processor 30 commands the motor-driven gradient syringe 64 to push the syringe plunger to dispense the held volume of gradient solution from the syringe to the waste reservoir 98 at a predetermined flow rate (e.g., 10 ml/minute). The flow rate of gradient solution dispensed from the syringe barrel is chosen so that the passages of the solution delivery assembly 32 and the sample delivery assembly 34 that carry the gradient solution are rinsed with gradient solution.

During a second operation, passages in the components of the solution delivery assembly 32 and the sample delivery assembly 34 that carry the buffer solution are purged of foreign materials. The processor 30 commands the solution delivery assembly manifold stopcocks 52, 54, 56 to rotate so that port 48 is in communication with port 46. The processor 30 then commands the motor-driven buffer syringe 68 to pull the syringe plunger to aspirate a predetermined volume (e.g., 20 ml) of buffer from the buffer reservoir 66. The volume of buffer solution aspirated into the syringe barrel should be sufficient to fill the passages in the components of the solution delivery assembly 32 and the sample delivery assembly 34 that carry the buffer solution. Once an appropriate volume of buffer solution is aspirated, the processor 30 commands the stopcocks 52, 54, 56 of the solution delivery assembly 32 to rotate so that port 48 is in communication with the outlet port 50. The stopcocks 82, 84, 86 of the sample delivery assembly 34 remain in their prior positions so that port 72 is in communication with port 78. Once these connections are made, the processor 30 commands the motor-driven buffer syringe 66 to push the syringe plunger to dispense the held volume of buffer solution from the syringe to the waste reservoir 98 at a predetermined flow rate (e.g., 35 ml/minute). The flow rate of buffer solution dispensed from the syringe barrel is chosen so that the passages of the solution delivery assembly 32 and the sample delivery assembly 34 that carry the buffer solution are thoroughly rinsed with buffer solution without over-pressurizing the components.

During a third operation, the rotor 24 of the ultracentrifuge 22 is filled with buffer solution. The processor 30 commands the solution delivery assembly manifold stopcocks 52, 54, 56 to rotate so that port 48 is in communication with port 46. The processor 30 then commands the motor-driven buffer syringe 68 to pull the syringe plunger to aspirate a predetermined volume (e.g., 140 ml) of buffer solution from the buffer reservoir 66. The volume of buffer solution aspirated into the syringe barrel should be sufficient to fill the rotor 24 of the ultracentrifuge and passages in the components of the solution delivery assembly 32, and the sample delivery assembly 34 that carry the buffer solution, as well as passages in the components of the overflow management assembly 36 and those leading from this assembly to the waste reservoir 98. Once an appropriate volume of buffer solution is aspirated, the processor 30 commands the stopcocks 52, 54, 56 of the solution delivery assembly 32 to rotate so that port 48 is in communication with the outlet port 50. Further the processor 30 commands the stopcocks 82, 84, 86 of the sample delivery assembly 34 to rotate so that port 72 is in communication with outlet port 80, the stopcocks 122, 124, 126 of the fraction collection assembly 36 to rotate so that port 112 is in communication with outlet port 120, and the stopcocks 152, 154, 156 of the overflow management assembly 38 to rotate so that port 142 is in communication with port 148 leading to the waste reservoir 98. Once these connections are made, the processor 30 commands the motor-driven buffer syringe 66 to push the syringe plunger to dispense the held volume of buffer solution from the syringe to the rotor 24 at a predetermined flow rate (e.g., a flow rate between about 5 ml/minute and about 35 ml/minute). The flow rate of buffer solution dispensed from the syringe barrel is chosen, so that the passages of the solution delivery assembly 32 and the sample delivery assembly 34 that carry the buffer solution are not over-pressurized. As will be appreciated by those skilled in the art, the operation of filling the ultracentrifuge rotor 24 with buffer solution may be accomplished using a smaller syringe by repeating the sequence of steps described above until a volume of buffer solution equal to that described above is delivered to the system components. For example, if a 100 ml capacity buffer syringe 68 were used and the volume of buffer solution needed was determined to be 140 ml, the syringe could be filled to 100 ml during a first sequence and 40 ml during a second sequence. Alternatively, the syringe could be filled to 70 ml during both sequences.

During a fourth operation, the system is de-bubbled. The processor 30 commands the solution delivery assembly manifold stopcocks 52, 54, 56 to rotate so that port 48 is in communication with port 46. The processor 30 the commands the motor-driven buffer syringe 68 to pull the syringe plunger to aspirate a predetermined volume (e.g., 80 ml) of buffer solution from the buffer reservoir 66. The volume of buffer solution aspirated into the syringe barrel should be sufficient to compensate for an increase in rotor 24 size due to rotation and a loss in air. Once an appropriate volume of buffer solution is aspirated, the processor 30 commands the stopcocks 52, 54, 56 of the solution delivery assembly 32 to rotate so that port 48 is in communication with the outlet port 50. The stopcocks 82, 84, 86 of the delivery assembly 34 remain in their prior positions so that port 72 is in communication with outlet port 80, the stopcocks 122, 124, 126 of the fraction collection assembly 36 remain in their prior positions so that port 112 is in communication with outlet port 120, and the stopcocks 152, 154, 156 of the overflow management assembly 38 remain in their prior positions so that port 142 is in communication with port 148 leading to the waste reservoir 98. Once these connections are made, the processor 30 commands the ultracentrifuge 22 to rotate the rotor 24 at a predetermined speed (e.g., 20,000 rpm). The processor 30 may also command the ultracentrifuge to use a predetermined final ramp speed (e.g., 100 rpm) and a predetermined coast speed (e.g., 500 rpm). As will be appreciated by those skilled in the art, when the ultracentrifuge 22 is accelerating, it initially accelerates at a slower rate (e.g., 4 rpm/second), and then a faster rate (e.g., 54 rpm/second). The final ramp speed is the speed at which the ultracentrifuge speeds up from the slower acceleration rate to the faster acceleration rate. Likewise, when the ultracentrifuge 22 is decelerating, it initially decelerates at a faster rate until it reaches the coast speed. The processor 30 may also activate a chiller surrounding the ultracentrifuge 22 to cool the components of the ultracentrifuge. When the rotor 24 reaches a predetermined intermediate speed (e.g., 5000 rpm), the processor commands the motor driven buffer syringe 66 to push the syringe plunger to dispense the held volume of buffer solution from the syringe to the rotor 24 at a predetermined flow rate (e.g., 5 ml/minute). The flow rate of buffer solution dispensed from the syringe barrel is chosen so that the solution is gently introduced without turbulence to reduce the potential for introduction of bubbles into the system. The solution introduced during this step compensates for air that is driven from the system and for an increase in rotor volume caused by its high rotational speed. The processor 30 maintains the rotor speed at the predetermined speed (e.g., 20,000 rpm) for a predetermined time (e.g., 3 minutes) selected so that the air is separated from the solution and driven out of the rotor. After the predetermined time, the processor commands the ultracentrifuge to brake.

During a fifth operation, the rotor 24 of the ultracentrifuge 22 is partially filled with gradient solution. The processor 30 commands the solution delivery assembly manifold stopcocks 52, 54, 56 to rotate so that port 42 is in communication with port 44. The processor 30 then commands the motor-driven gradient syringe 64 to pull the syringe plunger to aspirate a predetermined volume (e.g., 50 ml) of gradient solution from the gradient reservoir 62. The volume of gradient solution aspirated into the syringe barrel should be equal to a predetermine portion of the ultracentrifuge rotor 24 (e.g., about half of the rotor volume). Once an appropriate volume of gradient solution is aspirated, the processor 30 commands the stopcocks 52, 54, 56 of the solution delivery assembly 32 to rotate so that port 44 is in communication with the outlet port 50. The stopcocks 82, 84, 86 of the sample delivery assembly 34 remain in their prior positions so that port 72 is in communication with the outlet port 80, the stopcocks 122, 124, 126 of the fraction collection assembly 36 remain in their prior positions so that port 112 is in communication with outlet port 120, and the stopcocks 152, 154, 156 of the overflow management assembly 38 remain in their prior positions so that port 142 is in communication with port 148 leading to the waste reservoir 98. Once these connections are made, the processor 30 commands the motor-driven gradient syringe 64 to push the syringe plunger to dispense the held volume of gradient solution from the syringe toward the rotor 24 at a predetermined flow rate (e.g., 10 ml/minute). The flow rate of gradient solution dispensed from the syringe barrel is chosen so that the solution is gently introduced without turbulence to reduce the potential for introduction of bubbles into the system.

During a sixth operation, the gradient solution is chased with buffer solution so that substantially all of the gradient solution is in the rotor 24 of the ultracentrifuge 22, and the rotor has the predetermined portion filled with gradient solution. The processor 30 commands the solution delivery assembly manifold stopcocks 52, 54, 56 to rotate so that port 48 is in communication with port 46. The processor 30 then commands the motor-driven buffer syringe 68 to pull the syringe plunger to aspirate a predetermined volume (e.g., 20 ml) of buffer solution from the buffer reservoir 66. The volume of buffer solution aspirated into the syringe barrel should be sufficient to displace all of the gradient solution in the passages between the solution delivery assembly 32 and the rotor 24. The stopcocks 82, 84, 86 of the sample delivery assembly 34 remain in their prior positions so that port 72 is in communication with outlet port 80, the stopcocks 122, 124, 126 of the fraction collection assembly 36 remain in their prior positions so that port 112 is in communication with outlet port 120, and the stopcocks 152, 154, 156 of the overflow management assembly 38 remain in their prior positions so that port 142 is in communication with port 148 leading to the waste reservoir 98. Once these connections are made, the processor 30 commands the motor-driven buffer syringe 66 to push the syringe plunger to dispense the held volume of buffer solution from the syringe to the rotor 24 at a predetermined flow rate (e.g., 10 ml/minute). The flow rate of gradient solution dispensed from the syringe barrel is chosen so that the solution is gently introduced without turbulence to reduce the potential for introduction of bubbles into the system.

The rotor 24 is now filled with buffer solution and gradient solution. During a seventh operation, the processor 30 commands the ultracentrifuge 22 to rotate the rotor 24 at a predetermined speed (e.g., 20,000 rpm). The processor 30 may also command the ultracentrifuge to use a predetermined final ramp speed (e.g., 3500 rpm) and a predetermined coast speed (e.g., 7000 rpm). The ramp speed and coast speed should be selected so that the solutions gently transition from horizontal separation to vertical separation and back. Thus, the solutions are not mixed as the rotor 24 accelerates to and decelerations from the predetermined speed. As the rotor 24 is accelerating to the predetermined speed, passages in the sample delivery assembly 34 are purged. The processor 30 commands the solution delivery assembly manifold stopcocks 52, 54, 56 to rotate so that port 48 is in communication with port 46. The processor 30 then commands the motor-driven buffer syringe 68 to pull the syringe plunger to aspirate a predetermined volume (e.g., 40 ml) of buffer solution from the buffer reservoir 66. The volume of buffer solution aspirated into the syringe barrel should be sufficient to fill corresponding passages in the sample deliver assembly 34 and the fraction collection assembly 36 as will be apparent below. Once an appropriate volume of buffer solution is aspirated, the processor 30 commands the stopcocks 52, 54, 56 of the solution delivery assembly 32 to rotate so that port 48 is in communication with the outlet port 50. Further, the processor 30 commands the stopcocks 82, 84, 86 of the sample delivery assembly 34 to rotate so that port 72 is in communication with outlet port 80, the stopcocks 122, 124, 126 of the fraction collection assembly 36 to rotate so that port 112 is in communication with port 114. Once these connections are made, the processor 30 commands the motor-driven buffer syringe 66 to push the syringe plunger to dispense the held volume of buffer solution from the syringe into the priming accumulator 134 at a predetermined flow rate (e.g., 35 ml/minute). Once the buffer solution is dispensed, the processor 30 commands the stopcocks 82, 84, 86 of the sample delivery assembly 34 to rotate so that port 74 is in communication with outlet port 80. Once these connections are made, the processor 30 commands the peristaltic sample pump 94 to run in reverse for a predetermined period (e.g., one minute) at a predetermined flow rate (e.g., 30 ml/minute) to draw the buffer material from the priming accumulator 134 so the sample delivery passages are primed.

As the rotor 24 continues to accelerate to the predetermined speed, passages in the sample delivery assembly 34 used to recycle the sample solution are purged. The processor 30 commands the solution delivery assembly manifold stopcocks 52, 54, 56 to rotate so that port 48 is in communication with port 46. The processor 30 then commands the motor-driven buffer syringe 68 to pull the syringe plunger to aspirate a predetermined volume (e.g., 40 ml) of buffer solution from the buffer reservoir 66. The volume of buffer solution aspirated into the syringe barrel should be sufficient to fill corresponding the passages in the sample deliver assembly 34 and the fraction collection assembly 36 as will be apparent below. Once an appropriate volume of buffer solution is aspirated, the processor 30 commands the stopcocks 52, 54, 56 of the solution delivery assembly 32 to rotate so that port 48 is in communication with the outlet port 50. Further, the processor 30 commands the stopcocks 82, 84, 86 of the sample delivery assembly 34 to rotate so that port 72 is in communication with outlet port 80, the stopcocks 122, 124, 126 of the fraction collection assembly 36 to rotate so that port 112 is in communication with port 114. Once these connections are made, the processor 30 commands the motor-driven buffer syringe 66 to push the syringe plunger to dispense the held volume of buffer solution from the syringe into the priming accumulator 134 at a predetermined flow rate (e.g., 35 ml/minute). Once the suffer solution is dispensed, the processor 30 commands the stopcocks 82, 84, 86 of the sample delivery assembly 34 to rotate so that port 74 is in communication with outlet port 80. Once these connections are made, the processor 30 commands the peristaltic recycle pump 96 to run in reverse for a predetermined period (e.g., one minute) at a predetermined flow rate (e.g., 30 ml/minute) to draw the buffer material from the priming accumulator 134 so the recycle passages are primed.

During an eighth operation, additional buffer solution is added to compensate for rotor growth at speed. The processor 30 commands the solution delivery assembly manifold stopcocks 52, 54, 56 to rotate so that port 48 is in communication with port 46. The processor 30 then commands the motor-driven buffer syringe 68 to pull the syringe plunger to aspirate a predetermined volume (e.g., 35 ml) of buffer solution from the buffer reservoir 66. The volume of buffer solution aspirated into the syringe barrel should be sufficient to compensate for rotor growth. Once an appropriate volume of buffer solution is aspirated, the processor 30 commands the stopcocks 52, 54, 56 of the solution delivery assembly 32 to rotate so that port 48 is in communication with the outlet port 50. Further, the processor 30 commands the stopcocks 82, 84, 86 of the sample delivery assembly 34 to rotate so that port 72 is in communication with outlet port 80, and the stopcocks 122, 124, 126 of the fraction collection assembly 36 to rotate so that port 112 is in communication with outlet port 120. Once the rotor 24 reaches a predetermined intermediate speed (e.g., 5000 rpm), the processor 30 commands the motor-driven buffer syringe 66 to push the syringe plunger to dispense the held volume of buffer solution from the syringe to the rotor 24 at a predetermined flow rate (e.g., 5 ml/minute). The flow rate of buffer solution dispensed from the syringe barrel is chosen so that the solution is gently introduced without turbulence to reduce the potential for introduction of bubbles into the system.

During a ninth operation, the sample solution is loaded into the ultracentrifuge rotor 24. Once the rotor 24 reaches another predetermined intermediate speed (e.g., 20,000 rpm), the processor 30 commands the sample delivery assembly manifold stopcocks 82, 84, 86 to rotate so that port 74 is in communication with outlet port 80. Once these connections are made, the processor 30 commands the peristaltic sample pump 94 to run in a forward direction at a predetermined flow rate (e.g., 10 ml/minute) to dispense sample solution into the ultracentrifuge rotor 24. After a predetermined period (e.g., two minutes), the processor 30 commands overflow management assembly manifold stopcocks 152, 154, 156 to rotate so that port 142 is in communication with port 146. This allows solution leaving the ultracentrifuge rotor 24 (i.e., eluent) to be collected in the recycle reservoir 102.

During a tenth operation, the sample solution is chased with buffer solution so that substantially all of the sample solution enters the rotor 24 of the ultracentrifuge 22. The processor 30 commands the solution delivery assembly manifold stopcocks 52, 54, 56 to rotate so that port 48 is in communication with port 46. The processor 30 then commands the motor-driven buffer syringe 68 to pull the syringe plunger to a predetermined volume (e.g., 80 ml) of buffer solution from the buffer reservoir 66. The volume of buffer solution aspirated into the syringe barrel should be sufficient to displace all of the sample solution in the passages between the sample delivery assembly 34 and the rotor 24. Once an appropriate volume of buffer solution is aspirated, the processor 30 commands the stopcocks 52, 54, 56 of the solution delivery assembly 32 to rotate so that port 48 is in communication with the outlet port 50. When the sample reservoir 100 is empty, the processor 30 commands the sample delivery assembly manifold stopcocks 82, 84, 86 to rotate so that port 72 is in communication with outlet port 80. Further, the processor 30 stops the peristaltic sample pump 94, and the processor 30 commands the motor-driven buffer syringe 66 to push the syringe plunger to dispense the held volume of buffer solution from the syringe toward the rotor 24 at a predetermined flow rate (e.g., 5 ml/minute). The processor 30 then commands the ultracentrifuge to increase the rotor speed to a predetermined separation speed (e.g., 35,000 rpm).

After a predetermined period (e.g., eight minutes) at the separation speed, an eleventh operation is commences in which the collected eluent is recycled through the ultracentrifuge rotor 24. The processor 30 commands the overflow management assembly manifold stopcocks 152, 154, 156 to rotate so that port 142 is in communication with port 148 so that the rotor output is sent to the waste reservoir 98. Further, the processor 30 commands the sample delivery assembly manifold stopcocks 82, 84, 86 to rotate so that port 76 is in communication with outlet port 80. Once these connections are made, the processor 30 commands the peristaltic recycle pumps 96 to run in a forward direction at a predetermined flow rate (e.g., 10 ml/minute) to draw the recycled eluent from the recycle reservoir 96. After the recycle pump 96 has been running for a predetermined period (e.g., four minutes), the processor 30 commands the overflow management assembly manifold stopcocks 152, 154, 156 to rotate so that port 142 is in communication with the outlet port 150 so that the rotor output is sent to the final flow reservoir 160. The processor 30 commands the solution delivery assembly manifold stopcocks 52, 54, 56 to rotate so that port 48 is in communication with port 46. The processor 30 then commands the motor-driven buffer syringe 68 to pull the syringe plunger to aspirate a predetermined volume (e.g., 80 ml) of buffer solution from the buffer reservoir 66. The volume of buffer solution aspirated into the syringe barrel should be sufficient to displace all of the sample solution in the passages between the sample delivery assembly 34 and the rotor 24. Once an appropriate volume of buffer solution is aspirated, the processor 30 commands the stopcocks 52, 54, 56 of the solution delivery assembly 32 to rotate so that port 48 is in communication with the outlet port 50. When the recycle reservoir 102 is empty, the processor 30 commands the sample delivery assembly manifold stopcocks 82, 84, 86 to rotate so that port 72 is in communication with outlet port 80. Further, the processor 30 stops the recycle pump 94, and the processor 30 commands the motor-driven buffer syringe 66 to push the syringe plunger to dispense the held volume of buffer solution from the syringe toward the rotor 24 at a predetermined flow rate (e.g., 5 ml/minute). After a predetermined period (e.g., four minutes), the processor 30 commands the overflow management assembly manifold stopcocks 152, 154, 156 to rotate so that port 142 is in communication with port 148 so that the rotor output is sent to the waste reservoir 98. The processor 30 commands the solution delivery assembly manifold stopcocks 52, 54, 56 to rotate so that port 48 is in communication with port 46. After a predetermined separation period (e.g., two hours), the processor 30 stops the ultracentrifuge rotor rotation. As the ultracentrifuge rotor 24 stops rotating, less buoyant particles move to the bottom of the rotor and more buoyant particles move to the top of the rotor.

During a twelfth operation, particles are removed from the bottom of the rotor 24. As will be appreciated less buoyant particles will be removed before more buoyant particles. The processor 30 commands the motor driven stage of the fraction collector 132 to move to a home position. The processor 30 then commands the lower stopcock 176 to rotate so port 182 is only connected to port 186, the upper stopcock 178 to rotate so port 190 is only connected to port 192, and the stopcock 152 of the overflow management assembly manifold 140 to rotate so port 142 is connected to port 144. This configuration results in pressure equalization in the ultracentrifuge rotor 24 and the central tube 170 of the fraction volume measurement assembly 130.

Once the pressures are equalized, the processor 30 commands the stage of the fraction collector 132 to align a first well of the collection receptacle so solution traveling through port 186 of the lower stopcock 176 will fall into the first well. When the first well is in position, the processor 30 commands the lower stopcock 176 to rotate so port 182 is only connected to port 184, and separated solution drains from the ultracentrifuge rotor 24 into the central tube 170 of the fraction volume measurement assembly 130. As the solution rises in the tube 170, it eventually crosses the level of the predetermined infrared transmitter and receiver (i.e., either 200, 204 or 202, 206) indicating a predetermined volume (e.g., 1 ml or 2 ml) is in the tube. When this level is detected, the processor 30 commands the lower stopcock 176 to rotate so port 182 is only connected to port 186 and the upper stopcock 178 to rotate so port 194 is only connected to port 190, allowing the source 198 to gently push the solution in the tube 170 into the well in the fraction collector receptacle. After a sufficient dwell time (e.g., two seconds), the processor 30 commands the upper stopcock 178 to rotate so port 194 is only connected to port 192, and commands the stage of the fraction collector 132 align a second well of the collection receptacle so solution traveling through port 186 of the lower stopcock 176 will fall into the second well. The measurement and dispensing steps are repeated until a predetermined number of wells (e.g., 96 wells) is filled with solution. After the predetermined number of wells is filled, the processor commands the stage of the fraction collector 132 to align a waste well of the collection receptacle so solution traveling through port 186 of the lower stopcock 176 will fall into the waste well. The measurement and dispensing steps are repeated until a level is not detected, indicating the rotor 24 is empty.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A fraction volume measurement assembly for measuring and dispensing a predetermined volume of a sample, said assembly comprising:
    a measurement tube having a lower end and an upper end, said lower end including an opening for permitting the sample to enter and leave the tube;
    a valve in communication with the opening in the lower end of the measurement tube for controlling flow of the sample into and out of the tube;
    an electromagnetic transmitter mounted on the tube for transmitting electromagnetic energy along a line;
    an electromagnetic receiver mounted on the tube opposite the transmitter and along the line of transmitted electromagnetic energy so that when an upper level of the sample in the tube is below the line, energy transmitted by the transmitter is received by the receiver and when an upper level of the sample in the tube is above the line, the transmitted energy is refracted so it is not received by the receiver, indicating the predetermined volume of the sample is present in the tube, wherein the valve comprises a first three-way servo-driven stopcock, wherein the first stopcock has a first port connected to the lower end of the measurement tube, a second port connectable to a fraction collection assembly manifold, and a third port connectable to a fraction collector;
    a second valve in communication with an opening in the upper end of the measurement tube, wherein the second valve comprises a second three-way servo-driven stopcock, and wherein the second stopcock has a first port connected to the upper end of the measurement tube, a second port connectable to a vent line, and a third port connectable to a low pressure gas source; and
    a base plate having a recess for separably receiving the measurement tube and the first and second stopcocks.

2. The fraction volume measurement assembly of claim 1, wherein the first and second stopcocks each comprise a lever, and wherein the fraction volume measurement assembly further comprises cups adapted to receive the levers on the first and second stopcocks, respectively, when positioned in the recess.

3. The fraction volume measurement assembly of claim 2, wherein the cups are rotatable.

4. The fraction volume measurement assembly of claim 1, wherein the electromagnetic transmitter comprises a pair of infrared transmitters provided on the measurement tube and wherein the electromagnetic receiver comprises a pair of corresponding infrared receivers provided opposite the pair of infrared transmitters.

5. The fraction volume measurement assembly of claim 4, wherein the pair of infrared transmitters and receivers comprise a first set configured to measure a first predetermined volume and a second set configured to measure a second predetermined volume.

6. A fraction volume measurement assembly for measuring and dispensing a predetermined volume of a sample, said assembly comprising:
    a measurement tube having a lower end and an upper end, the upper and lower ends each including an opening for permitting the sample to enter and leave the tube;
    a first valve comprising a first valve lever, the first valve is in communication with the opening in the lower end of the tube for controlling flow into and out of the tube based on a position of the first valve lever;
    a second valve comprising a second valve lever, the first valve is in communication with the opening in the upper end of the tube for controlling flow into and out of the tube based on a position of the second valve lever;
    a base plate having a recess, a first cup, and a second cup, the tube being separably received in the recess with the first and second valve levers being received by the first and second cups, respectively; and
    a mount adjacent to the tube and having an electromagnetic transmitter for transmitting electromagnetic energy along a line and an electromagnetic receiver opposite the transmitter and along the line of transmitted electromagnetic energy, the mount being positioned with respect to the recess so that the electromagnetic energy transmitted by the transmitter is received by the receiver except when the tube has sample above the line of electromagnetic energy indicating the predetermined volume of the sample is present in the tube.

7. The fraction volume measurement assembly of claim 6, wherein the base plate further comprises a clamp holding the tube in the recess with the first and second valve levers received by the first and second cups, respectively.

8. The fraction volume measurement assembly of claim 6, further comprising first and second servomotors mounted on a bracket connected to the base plate, the first and second servomotors rotating the first and second cups so as to change the position of the first and second valve levers, respectively.

9. The fraction volume measurement assembly of claim 6, further comprising a biasing device that biases the mount toward the tube.

10. The fraction volume measurement assembly of claim 6, further comprising an adjustment mechanism fixed to the mount, the adjustment mechanism being configured to adjust the line of the electromagnetic energy relative to the tube to permit adjustment of the predetermined volume.

11. The fraction volume measurement assembly of claim 6, wherein the first and second valves each comprises three-way servo-driven stopcocks.

12. The fraction volume measurement assembly of claim 11, wherein the first valve has a first port connected to the lower end of the tube, a second port connectable to a fraction collection assembly manifold, and a third port connectable to a fraction collector.

13. The fraction volume measurement assembly of claim 11, wherein the second valve has a first port connected to the upper end of the tube, a second port connectable to a vent line, and a third port connectable to a low pressure gas source.

* * * * *